United States Patent [19]

Misaki et al.

[11] Patent Number: 4,481,149
[45] Date of Patent: Nov. 6, 1984

[54] FLUORINE-CONTAINING PHENYL BENZOATE COMPOUNDS, AND THEIR PRODUCTION AND USE

[75] Inventors: Susumu Misaki, Minoo; Masahiro Suefuji, Settsu; Tamio Mitote, Kawanishi; Naotake Matsumura, Itami, all of Japan

[73] Assignee: Daikin Kogyo Co., Ltd., Osaka, Japan

[21] Appl. No.: 477,899

[22] Filed: Mar. 23, 1983

Related U.S. Application Data

[60] Division of Ser. No. 301,128, Sep. 11, 1981, Pat. No. 4,393,231, which is a continuation of Ser. No. 75,686, Sep. 14, 1979, abandoned.

[30] Foreign Application Priority Data

Sep. 19, 1978 [JP] Japan .................................. 53-115447
Nov. 21, 1978 [JP] Japan .................................. 53-144571

[51] Int. Cl.³ .......................... G09K 3/34; C02F 1/13; C07C 69/76; C07C 79/32; C07C 121/52
[52] U.S. Cl. .................. 260/465 D; 260/463; 350/350 R; 350/350 S; 560/109; 560/106; 560/61; 560/64; 560/72
[58] Field of Search ................ 252/299.5, 299.67; 350/350 R, 350 S; 560/61, 64, 72, 73, 106, 109; 260/465 D, 465 F, 465 G, 463

[56] References Cited

U.S. PATENT DOCUMENTS

| | | | |
|---|---|---|---|
| 3,876,286 | 4/1975 | Deutscher et al. | 252/299.67 |
| 3,923,857 | 12/1975 | Boller et al. | 252/299.67 |
| 3,960,752 | 6/1976 | Klamderman et al. | 252/299.67 |
| 4,001,137 | 1/1977 | Steinstrasser | 252/299.67 |
| 4,011,173 | 3/1977 | Steinstrasser | 252/299.67 |
| 4,086,002 | 4/1978 | Arora | 252/299.67 |
| 4,393,231 | 7/1983 | Misaki et al. | 252/299.67 |

OTHER PUBLICATIONS

Griffin, A. C. et al., JACS, vol. 100 (20), pp. 6329-6333, (Sep. 27, 1978).
CA., vol. 95, 124320k, (1981).
Griffin, A. C. et al., Mol. Cryst. Liq. Cryst., vol. 41 (Lett.), pp 141-144, (1978), (Feb.).
Titov, V. V. et al., Mol. Cryst. Liq. Cryst., vol. 41, pp. 1-5, (Aug. 1978).
Zverkova, T. I. et al., Advances in Liq. Cryst. Res. and Appl.; Bata, Lajos, Pergamon Press, Oxford, pp. 991-995, (1980).

*Primary Examiner*—Teddy S. Gron
*Attorney, Agent, or Firm*—Birch, Stewart, Kolasch & Birch

[57] ABSTRACT

Fluorine-containing phenyl benzoate compounds which have the general formula:

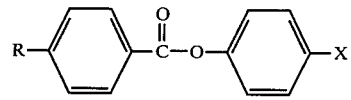

wherein R is a $C_1$-$C_{12}$ perfluoroalkyl group, a $C_1$-$C_{12}$ alkyl group, a $C_1$-$C_{12}$ alkoxy group, a $C_2$-$C_{13}$ alkanoyloxy group, a $C_2$-$C_{13}$ alkoxycarbonyl group, a $C_2$-$C_{13}$ alkoxycarbonyloxy group or a $C_2$-$C_{13}$ alkyldioxycarbonyl group and X is a $C_1$-$C_{12}$ alkyl group, a $C_1$-$C_{12}$ alkoxy group, a cyano group, a trifluoromethyl group or a nitro group with the proviso that X is trifluoromethyl when R is other than perfluoroalkyl are useful as components of liquid crystals.

11 Claims, No Drawings

FLUORINE-CONTAINING PHENYL BENZOATE COMPOUNDS, AND THEIR PRODUCTION AND USE

This application is a divisional of copending application Ser. No. 301,128, filed on Sept. 11, 1981, now U.S. Pat. No. 4,393,231 which is a Continuation of application Ser. No. 075,686, filed on Sept. 14, 1979, now abandoned.

The present invention relates to fluorine-containing phenyl benzoate compounds, and their production and use. More particularly, it relates to novel fluorine-containing phenyl benzoate compounds, a process for production thereof and their use for liquid crystal compositions.

Many liquid crystal compounds which are usable in indicating apparatuses are known. Among them, phenyl benzoate compounds of the formula:

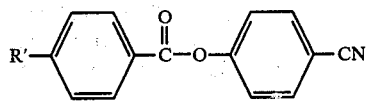

wherein R' is a $C_4$–$C_7$ alkyl group or a $C_4$–$C_7$ alkoxy group are chemically stable, colorless materials showing a large positive induction anisotropy due to the strong electron attracting property of the cyano group and have thus been employed widely as an indicating factor of FEM type. However, their stability is restricted because of the presence of a cyano group as the substituent. The electrical properties are also not satisfying.

It has now been found that, by introducing a trifluoromethyl group for the cyano group in the said phenyl benzoate compound or by introducing a perfluoroalkyl group into a phenylbenzoate compound having an electron attracting group such as cyano, trifluoromethyl or nitro group, the above mentioned defects can be improved. Namely, it has been found that, when some kinds of phenyl benzoate compounds bearing a trifluoromethyl group and/or a perfluoroalkyl group on the benzene ring(s) are employed as a component of a liquid crystal composition, the stability and the electrical properties are greatly improved.

The fluorine-containing phenyl benzoate compounds usable in the present invention are representable by the formula:

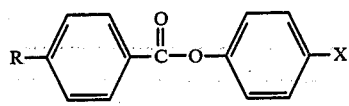

wherein R is a $C_1$–$C_{12}$ perfluoroalkyl group, a $C_1$–$C_{12}$ alkyl group, a $C_1$–$C_{12}$ alkoxy group, a $C_2$–$C_{13}$ alkanoyloxy group, a $C_2$–$C_{13}$ alkoxycarbonyl group, a $C_2$–$C_{13}$ alkoxycarbonyloxy group or a $C_2$–$C_{13}$ alkyldioxycarbonyl group and X is a $C_1$–$C_{12}$ alkyl group, a $C_1$–$C_{12}$ alkoxy group, a cyano group, a trifluoromethyl group or a nitro group with the proviso that X is trifluoromethyl when R is other than perfluoroalkyl.

Examples of the fluorine-containing phenyl benzoate compounds [I] are shown in Table 1.

TABLE 1

| R | X | Range of liquid crystal Temperature (MR) (°C.) |
|---|---|---|
| $C_4H_9$ | $CF_3$ | 67.8 (monotropic) |
| $C_5H_{11}$ | $CF_3$ | 66.8 (monotropic) |
| $C_6H_{13}$ | $CF_3$ | 58.8 (monotropic) |
| $C_7H_{15}$ | $CF_3$ | 61.0 (monotropic) |
| $C_8H_{17}$ | $CF_3$ | 58.5 (monotropic) |
| $C_4H_9O$ | $CF_3$ | 93.4 (monotropic) |
| $C_5H_{11}O$ | $CF_3$ | 78.5 (monotropic) |
| $C_6H_{13}O$ | $CF_3$ | 74.7–76.5 |
| $C_7H_{15}O$ | $CF_3$ | 62.9–74.3 |
| $C_8H_{15}O$ | $CF_3$ | 62.5–72.5 |
| $(CF_3)_2CFCF_2CF_2$ | CN | 90.0–98.5 |
| $(CF_3)_2CF(CF_2CF_2)_2$ | CN | 109.6–121.3 |
| $(CF_3)_2CF(CF_2CF_2)_3$ | CN | 130.7–140.7 |
| $C_6H_{13}$ | CN | 99.8–123.3 |
| $C_8F_{17}$ | CN | 118–145 |
| $C_8H_{17}$ | $CH_3$ | 111–112 (monotropic) |
| $(CF_3)_2CFCF_2CF_2$ | $C_5H_{11}$ | 57–58 (monotropic) |
| $(CF_3)_2CFCF_2CF_2$ | $CF_3$ | 67.5–68.7 (monotropic) |
| $(CF_3)_2CFCF_2CF_2$ | $NO_2$ | 68.6–79.2 |

The fluorine-containing phenyl benzoate compounds [I] can be prepared by reacting a p-substituted phenol of the formula:

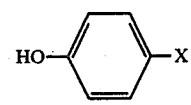

wherein X is as defined above or its reactive derivative with a p-substituted benzoic acid of the formula:

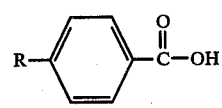

wherein R is as defined above or its reactive derivative according to a per se conventional esterification procedure.

As the reactive derivative of the p-substituted phenol [II], there may be used its alkali metal salt (e.g. sodium salt, potassium salt). As the reactive derivative of the p-substituted benzoic acid [III], there may be exemplified acid halide (e.g. acid chloride, acid bromide), acid anhydride, etc. Depending on the kind of the by-product in the reaction, the use of an acid-accepting agent or a dehydrating agent is preferred. For instance, in the reaction between the p-substituted phenol [II] and the acid halide of the p-substituted benzoic acid [III], the presence of an acid-accepting agent is favorable. Further, for instance, in the reaction between the p-substituted phenol [II] and the p-substituted benzoic acid [III], the presence of a dehydrating agent is preferable. Examples of the acid-accepting agents are, inorganic bases such as sodium hydroxide and sodium carbonate, organic bases such as pyridine and triethylamine, etc. The dehydrating agents are, for example, phosphorus pentoxide, anhydrous zinc chloride, metaphosphoric acid, polyphosphoric acids, aromatic sulfonic acids, etc. The reaction is usually effected in an inert solvent (e.g. ether, benzene, carbon tetrachloride) at room temperature or if necessary, under heating.

The thus prepared fluorine-containing phenyl benzoate compounds [I] are useful as a component of liquid crystal compositions. For example, one or more of them are admixed with any other liquid crystal material by a per se conventional procedure, whereby the stability and the electrical properties can be greatly improved. Owing to the high stability, such liquid crystal compositions can be used for a long time without being influenced by the conditions of the environment.

In addition to the usefulness as a component of liquid crystal compositions, the fluorine-containing phenyl benzoate compounds [I] show an interesting activity as a physiologically active substance.

The present invention will be explained further in detail by the following Examples.

EXAMPLE 1

A mixture of p-n-butylbenzoyl chloride (3.0 g, 15.3 mmol) and p-trifluoromethylphenol (2.48 g, 15.3 mmol) in anhydrous benzene (15 ml) is stirred at room temperature for 3 hours in the presence of anhydrous pyridine (5 ml) under nitrogen stream and then heated at 50° C. for 4 hours. After cooling, the reaction mixture is filtered under nitrogen stream, and the filtrated is concentrated to dryness under reduced pressure to yield crude p'-trifluoromethylphenyl p-n-butylbenzoate (3.65 g). The crude product is recrystallized from ethanol, and the resultant crystals are dissolved in benzene, treated with active alumina and further recrystallized from methanol twice to obtain a purified product, m.p. 67.8° C.

| Elementary analysis: | C % | H % |
| --- | --- | --- |
| Calculated: | 67.08 | 5.28 |
| Found: | 67.13 | 5.04 |

EXAMPLE 2

A mixture of p-n-pentylbenzoyl chloride (12.7 g, 60.4 mmol) and p-trifluoromethylphenol (12.0 g, 74.1 mmol) in anhydrous benzene (30 ml) is treated as in Example 1 in the presence of anhydrous pyridine (15 ml) to yield crude p'-trifluoromethylphenyl p-n-pentylbenzoate (12.8 g), which is purified as in Example 1. The thus purified product shows a melting point of 66.8° C.

| Elementary analysis: | C % | H % |
| --- | --- | --- |
| Calculated: | 67.86 | 5.65 |
| Found: | 67.77 | 5.51 |

EXAMPLE 3

A mixture of p-n-hexylbezoyl chloride (13.9 g, 62 mmol) and p-trifluoromethylphenol (10.0 g, 61.8 mmol) in anhydrous benzene (30 ml) is treated as in Example 1 in the presence of anhydrous pyridine (10 ml) to yield crude p'-trifluoromethylphenyl p-n-hexylbenzoate (11.4 g), which is purified as in Example 1. The melting point of the thus purified product is 58.8° C.

| Elementary analysis: | C % | H % |
| --- | --- | --- |
| Calculated: | 68.57 | 5.28 |
| Found: | 68.39 | 5.45 |

EXAMPLE 4

A mixture of p-n-heptylbenzoyl chloride (11.67 g, 48.9 mmol) and p-trifluoromethylphenol (7.45 g, 46.0 mmol) in anhydrous benzene (30 ml) is treated as in Example 1 in the presence of anhydrous pyridine (15 ml) to yield crude p'-trifluoromethylphenyl p-n-heptylbenzoate (11.39 g), which is purified as in Example 1. The melting point of the thus purified product is 61.0° C.

| Elementary analysis: | C % | H % |
| --- | --- | --- |
| Calculated: | 69.23 | 6.32 |
| Found: | 69.13 | 6.23 |

EXAMPLE 5

A mixture of p-n-octylbenzoyl chloride (12.54 g, 49.7 mmol) and p-trifluoromethylphenol (8.03 g, 49.6 mmol) is treated as in Example 1 in the presence of anhydrous pyridine to yield crude p'-trifluoromethylphenyl p-n-octylbenzoate (13.26 g), which is purified as in Example 1. The melting point of the thus purified product is 58.5° C.

| Elementary analysis: | C % | H % |
| --- | --- | --- |
| Calculated: | 69.84 | 6.61 |
| Found: | 69.70 | 6.49 |

EXAMPLE 6

A mixture of p-n-octylbenzoic acid (4.68 g, 20 mmol) and p-trifluoromethylphenol (3.24 g, 20 mmol) in benzene (50 ml) is refluxed in the presence of phosphorus pentoxide (5.0 g) for 5 hours to yield p'-trifluoromethylphenyl p-n-octylbenzoate (6.0 g), m.p. 58.5° C.

| Elementary analysis: | C % | H % |
| --- | --- | --- |
| Calculated: | 69.84 | 6.61 |
| Found: | 69.70 | 6.46 |

EXAMPLE 7

The reaction between p-n-pentyloxybenzoyl chloride (10.2 g, 45 mmol) and p-trifluoromethylphenol (7.24 g, 45 mmol) is effected as in Example 4 to yield crude p'-trifluoromethylphenyl p-n-pentyloxybenzoate (11.5 g), which is purified as in Example 1. The melting point of the thus purified product is 78.5° C.

| Elementary analysis: | C % | H % |
| --- | --- | --- |
| Calculated: | 64.59 | 5.38 |
| Found: | 64.82 | 5.24 |

EXAMPLE 8

The reaction between p-n-hexyloxybenzoyl chloride (14.9 g, 62 mmol) and p-trifluoromethylphenol (10.0 g, 61.8 mmol) is effected as in Example 4 to yield crude p'-trifluoromethylphenyl p-n-hexyloxybenzoate (16.2 g), which is purified as in Example 1. MR, 74.7°–76.5° C.

| Elementary analysis: | C % | H % |
|---|---|---|
| Calculated: | 65.57 | 5.74 |
| Found: | 65.45 | 5.59 |

EXAMPLE 9

The reaction between p-n-heptyloxybenzoyl chloride (11.59 g, 45.6 mmol) and p-trifluoromethylphenol (7.38 g, 45.6 mmol) is effected as in Example 4 to yield crude p′-trifluoromethylphenyl p-n-heptyloxybenzoate (12.8 g), which is purified as in Example 1. MR, 62.9°–74.3° C.

| Elementary analysis: | C % | H % |
|---|---|---|
| Calculated: | 66.32 | 6.08 |
| Found: | 65.60 | 5.96 |

EXAMPLE 10

The reaction between p-n-octyloxybenzoyl chloride (15.04 g, 56.1 mmol) and p-trifluoromethylphenol (9.01 g, 55.7 mmol) is effected as in Example 4 to yield crude p′-trifluoromethylphenyl p-n-octyloxybenzoate (13.7 g), which is purified as in Example 1. MR, 62.5°–72.5° C.

| Elementary analysis: | C % | H % |
|---|---|---|
| Calculated: | 67.01 | 6.35 |
| Found: | 66.89 | 6.18 |

EXAMPLE 11

The reaction of p-acetoxybenzoyl chloride (10.99 g, 55.4 mmol) and p-trifluoromethylphenol (8.97 g, 55.4 mmol) is effected as in Example 4 to obtain crude p′-trifluoromethylphenyl p-acetoxybenzoate (8.72 g), which is purified as in Example 1, m.p. 143° C.

| Elementary analysis: | C % | H % |
|---|---|---|
| Calculated: | 59.26 | 3.40 |
| Found: | 59.04 | 3.21 |

EXAMPLE 12 p′-Cyanophenyl p-(3-trifluoromethylperfluorobutyl)benzoate (a) p-(3-Trifluoromethylperfluorobutyl)benzoic acid A mixture of 3-trifluoromethylperfluorobutyl iodide (19.5 g, 50 mmol), p-iodobenzoic acid (12.4 g, 50 mmol), activated copper (15.9 g, 250 mmol) and dried dimethyl sulfoxide (100 ml) is stirred at 130° C. in an autoclave for 14.5 hours. After cooling, the reaction mixture is poured into water (400 ml), and the precipitated solid material is collected by filtration and dried. Then, the solid material is extracted with ethanol (200 ml), and the ethanol extract is concentrated to yield crude p-(3-trifluoromethylperfluorobutyl)benzoic acid (5.8 g). The crude product is recrystallized from ethanol-water. The melting point of the purified product is 189°–190° C.

| Elementary analysis: | C % | H % | F % |
|---|---|---|---|
| Calculated: | 36.92 | 1.28 | 53.59 |
| Found: | 36.50 | 1.55 | 53.54 |

(b) p-(3-Trifluoromethylperfluorobutyl)benzoyl chloride

A mixture of p-perfluoroalkylbenzoic acid (8.1 g, 20 mmol) prepared in (a) and thionyl chloride (35 ml) is refluxed for 3 hours. Distillation of the reaction mixture affords p-(3-trifluoromethylperfluorobutyl)benzoyl chloride (5.8 g), b.p. 79°–81° C./0.8 mm Hg.

| Elementary analysis: | C % | H % |
|---|---|---|
| Calculated: | 35.25 | 0.98 |
| Found: | 35.50 | 0.80 |

(c) p′-Cyanophenyl p-(3-trifluoromethylperfluorobutyl)benzoate

A mixture of p-(3-trifluoromethylperfluorobutyl)benzoyl chloride (4.86 g, 11.9 mmol), p-cyanophenol (1.38 g, 11.6 mmol), anhydrous benzene (20 ml) and anhydrous pyridine (20 ml) is stirred at room temperature for 4 hours under nitrogen stream and heated at 50° C., for 4 hours. After cooling, the reaction mixture is filtered under nitrogen stream, and the filtrate is concentrated to dryness under reduced pressure to yield crude p′-cyanophenyl p-(3-trifluoromethylperfluorobutyl)benzoate (5.5 g). The crude product is recrystallized from ethanol. MR, 90.0°–98.5° C.

| Elementary analysis: | C % | H % | N % | F % |
|---|---|---|---|---|
| Calculated: | 46.44 | 1.63 | 2.85 | 53.59 |
| Found: | 46.20 | 1.38 | 2.97 | 53.54 |

EXAMPLE 13

(a) A mixture of p-iodobenzoic acid (4.96 g, 20 mmol), $(CF_3)_2CF(CF_2CF_2)_2I$ (9.92 g, 20 mmol), copper (6.36 g, 50 mmol) and dimethyl sulfoxide (40 ml) is treated as in Example 12(a) to yield

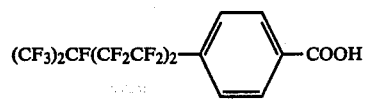

(5.52 g), m.p. 195°–198° C.

| Elementary analysis: | C % | H % | F % |
|---|---|---|---|
| Calculated: | 34.36 | 0.82 | 58.16 |
| Found: | 34.53 | 0.85 | 58.15 |

(b) The reaction of

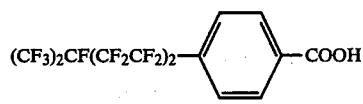

(9.3 g, 19 mmol) prepared in (a) with thionyl cloride (55 ml) is effected as in Example 12(b) to yield

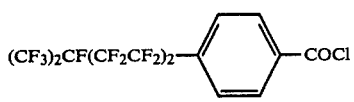

(8.35 g), b.p. 106° C./2 mm Hg.

| Elementary analysis: | C % | H % |
|---|---|---|
| Calculated: | 33.04 | 0.79 |
| Found: | 32.89 | 0.59 |

(c) A mixture of

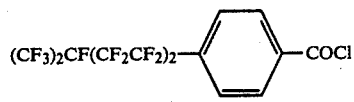

(2.54 g, 5 mmol) prepared in (b), p-cyanophenol (0.6 g, 5 mmol), benzene (10 ml) and pyridine (15 ml) is treated as in Example 12(c) to yield

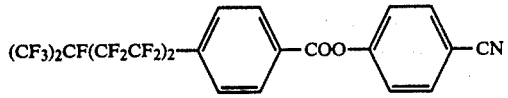

(2.50 g), MR, 109.6°–121.3° C.

| Elementary analysis: | C % | H % | F % |
|---|---|---|---|
| Calculated: | 40.61 | 1.35 | 2.37 |
| Found: | 42.63 | 1.08 | 2.54 |

EXAMPLE 14

(a) A mixture of p-iodobenzoic acid (24.8 g, 100 mmol), $(CF_3)_2CF(CF_2CF_2)_3I$ (59.6 g, 100 mmol), copper (12.7 g, 204 mmol) and dimethyl sulfoxide (250 ml) is treated as in Example 12(a) to yield

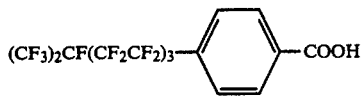

(9.0 g), m.p. 196°–198° C.

| Elementary analysis: | C % | H % |
|---|---|---|
| Calculated: | 32.54 | 0.85 |
| Found: | 32.49 | 0.63 |

(b) The reaction of

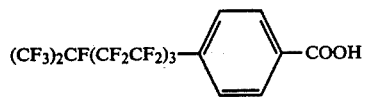

(6.0 g, 10 mmol) prepared in (a) with thionyl chloride (30 ml) is effected as in Example 12(b) to yield

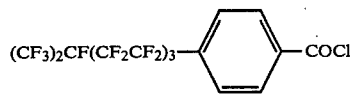

(2.17 g), b.p. 92°–103° C./2.0 mm Hg.

| Elementary analysis: | C % | H % |
|---|---|---|
| Calculated: | 31.55 | 0.66 |
| Found: | 31.72 | 0.54 |

(c) A mixture of

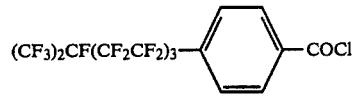

(1.78 g, 1.9 mmol) prepared in (b), p-cyanophenol (0.23 g, 1.9 mmol), benzene (10 ml) and pyridine (10 ml) is treated as in Example 12(c) to yield

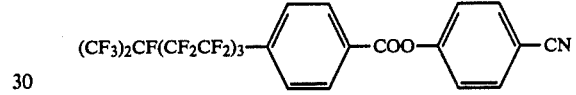

(1.50 g), MR, 130.7°–140.7° C.

| Elementary analysis: | C % | H % | N % |
|---|---|---|---|
| Calculated: | 38.21 | 1.16 | 2.03 |
| Found: | 39.91 | 0.85 | 2.25 |

EXAMPLE 15

(a) A mixture of p-iodobenzoic acid (24.8 g, 100 mmol), $C_6F_{13}I$ (52.2 g, 117 mmol), copper (31.8 g, 500 ml) and dimethyl sulfoxide (250 ml) is treated as in Example 12(a) to yield

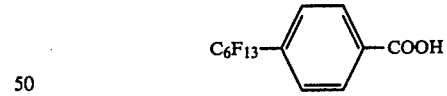

(6.9 g), m.p. 196°–198° C.

| Elementary analysis: | C % | H % | F % |
|---|---|---|---|
| Calculated: | 37.45 | 1.14 | 53.14 |
| Found: | 37.35 | 1.00 | 53.40 |

(b) The reaction of

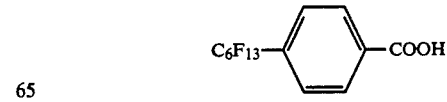

(6.4 g, 14.5 mmol) prepared in (a) with thionyl chloride (50 ml) is effected as in Example 12(b) to yield

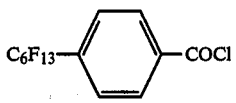

(40 g), b.p. 75° C./0.7 mm Hg.

| Elementary analysis: | C % | H % |
|---|---|---|
| Calculated: | 34.10 | 0.87 |
| Found: | 31.02 | 0.90 |

(c) A mixture of

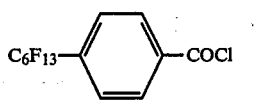

(3.48 g, 7.6 mmol) prepared in (b), p-cyanophenol (0.9 g, 7.6 mmol), benzene (20 ml) and pyridine (20 ml) is treated as in Example 12(c) to yield

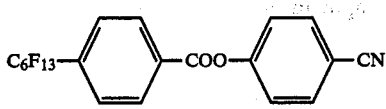

(3.90 g), MR, 99.8°–123.3° C.

| Elementary analysis: | C % | H % | N % | F % |
|---|---|---|---|---|
| Calculated: | 44.34 | 1.47 | 2.59 | 45.66 |
| Found: | 44.36 | 1.18 | 2.75 | 45.20 |

EXAMPLES 16 AND 17

(a) A mixture of p-iodobenzoic acid (18.7 g, 75 mmol), $C_8F_{17}I$ (43.2 g, 80 mmol), copper (19.1 g, 140 mmol) and dimethyl sulfoxide (120 ml) is treated as in Example 12(a) to yield

(16.0 g), m.p. 199°–200° C.

| Elementary analysis: | C % | H % |
|---|---|---|
| Calculated: | 33.33 | 0.93 |
| Found: | 33.09 | 0.73 |

(b) The reaction of

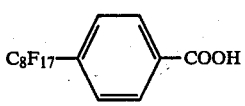

(26.0 g, 48.1 mmol) is prepared in (a) with thionyl chloride (120 ml) is effected as in Example 12(b) to yield

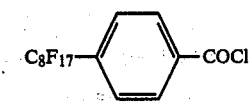

(18.7 g), b.p. 112°–114° C./1.0 mm Hg.

| Elementary analysis: | C % | H % |
|---|---|---|
| Calculated: | 32.29 | 0.72 |
| Found: | 32.14 | 0.70 |

(c) In Example 16, a mixture of

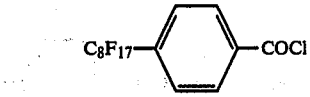

(3.45 g, 6.2 mmol) prepared in (b), p-cyanophenol (0.74 g, 6.2 mmol), benzene (20 ml) and pyridine (20 ml) is treated as in Example 12(c) to yield

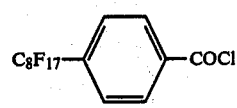

(3.7 g), MR, 118°–145° C.

| Elementary analysis: | C % | H % | N % |
|---|---|---|---|
| Calculated: | 41.19 | 1.25 | 2.18 |
| Found: | 41.02 | 0.96 | 2.40 |

In Example 17, a mixture of

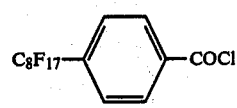

(3.11 g, 5.6 mmol), p-cresol (0.60 g, 5.6 mmol), benzene (20 ml) and pyridine (15 ml) is treated as in Example 12(c) to yield

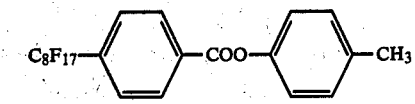

(3.5 g), MR, 111°–112° C. (monotropic).

| Elementary analysis: | C % | H % |
|---|---|---|
| Calculated: | 41.90 | 1.75 |
| Found: | 41.86 | 1.44 |

EXAMPLE 18

A mixture of

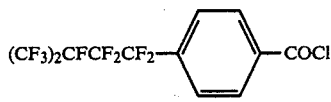

(2.86 g, 7 mmol) prepared in Example 12(b),

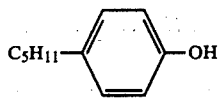

(1.19 g, 7 mmol), benzene (15 ml) and pyridine (5 ml) is treated as in Example 12(c) to yield

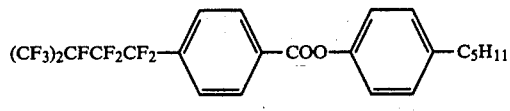

(3.2 g), MR, 57°–58° C. (monotropic).

| Elementary analysis: | C % | H % |
| --- | --- | --- |
| Calculated: | 51.49 | 3.54 |
| Found: | 51.41 | 3.24 |

EXAMPLE 19

A mixture of

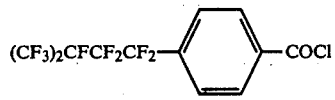

(3 g, 7.4 mmol) prepared in Example 12(b),

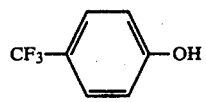

(1.2 g, 7.4 mmol), benzene (10 ml) and pyridine (10 ml) is treated as in Example 12(c) to yield

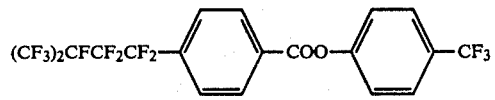

(3.91 g), MR, 67.5°–68.7° C. (monotropic).

| Elementary analysis: | C % | H % |
| --- | --- | --- |
| Calculated: | 42.70 | 0.01 |
| Found | 42.68 | 0.01 |

EXAMPLE 20

A mixture of

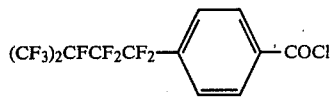

(1.85 g, 4.6 mmol) prepared in Example 12(b), p-nitrophenol (0.64 g, 4.6 mmol), benzene (10 ml) and pyridine (10 ml) is treated as in Example 12(c) to yield

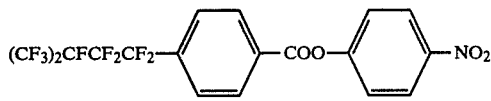

(2.02 g), MR, 68.6°–79.2° C.

| Elementary analysis: | C % | H % |
| --- | --- | --- |
| Calculated: | 42.27 | 0.02 |
| Found | 42.17 | 0.02 |

What is claimed is:

1. A compound of the formula:

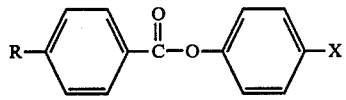

wherein R is a $C_1$–$C_{12}$ perfluoroalkyl group and X is a alkyl a cyano group or a nitro group.

2. The compound according to claim 1, which is

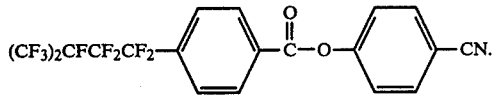

3. The compound according to claim 1, which is

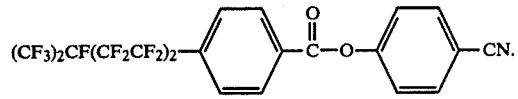

4. The compound according to claim 1, which is

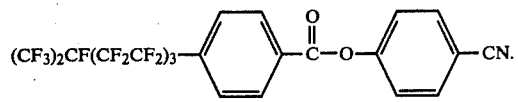

5. The compound according to claim 1, which is

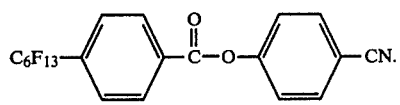

6. The compound according to claim 1, which is

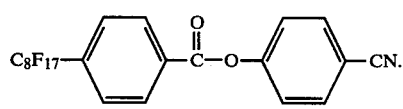
7. The compound which is
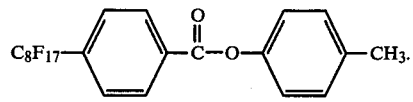
8. The compound which is
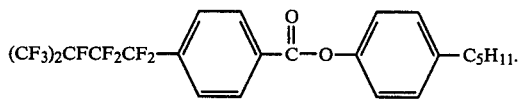
9. The compound according to claim 1, which is
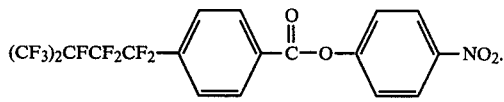
10. The compound according to claim 1, wherein X is a cyano group.
11. The compound according to claim 1, wherein X is a nitro group.
* * * * *